United States Patent
Warnock, Jr. et al.

(10) Patent No.: US 12,064,565 B2
(45) Date of Patent: Aug. 20, 2024

(54) FILAMENT WRAPPING AND REFLOW SYSTEM AND METHODS TO MANUFACTURE AN ELONGATE MEDICAL DEVICE

(71) Applicant: Medtronic, Inc., Minneapolis, MN (US)

(72) Inventors: Kenneth D. Warnock, Jr., Manchester-by-the-Sea, MA (US); Dale F. Seeley, Spring Park, MN (US); Jonathan E. Baxter, Minneapolis, MN (US); Gonzalo Martinez, Mendota Heights, MN (US)

(73) Assignee: Medtronic, Inc., Minneapolis, MN (US)

( * ) Notice: Subject to any disclaimer, the term of this patent is extended or adjusted under 35 U.S.C. 154(b) by 481 days.

(21) Appl. No.: 17/162,101

(22) Filed: Jan. 29, 2021

(65) Prior Publication Data
US 2021/0236767 A1    Aug. 5, 2021

Related U.S. Application Data

(60) Provisional application No. 62/970,561, filed on Feb. 5, 2020.

(51) Int. Cl.
A61M 25/00    (2006.01)

(52) U.S. Cl.
CPC .... *A61M 25/0012* (2013.01); *A61M 25/0053* (2013.01); *A61M 2025/0058* (2013.01); *A61M 2205/36* (2013.01)

(58) Field of Classification Search
CPC ...... A61M 2205/36; A61M 2025/0058; A61M 25/0053; A61M 25/0012
See application file for complete search history.

(56) References Cited

U.S. PATENT DOCUMENTS

| | | |
|---|---|---|
| 4,637,396 A | 1/1987 | Cook |
| 9,974,887 B2 | 5/2018 | Eversull et al. |
| 2008/0262472 A1 | 10/2008 | Lunn et al. |
| 2016/0303347 A1* | 10/2016 | Porter .................. B29C 48/157 |
| 2017/0182290 A1* | 6/2017 | Stern .................. A61M 25/005 |
| 2018/0289925 A1 | 10/2018 | Palmer et al. |
| 2020/0391009 A1 | 12/2020 | Martin |
| 2021/0001079 A1 | 1/2021 | Martin |

(Continued)

FOREIGN PATENT DOCUMENTS

| | | |
|---|---|---|
| WO | 98/07523 | 2/1998 |
| WO | 2016/168505 | 10/2016 |
| WO | WO 2020/257125 A1 | 12/2020 |

OTHER PUBLICATIONS

International Search Report and Written Opinion from PCT Application No. PCT/US2021/016298 dated Jul. 12, 2021, 18 pages.

*Primary Examiner* — Vishal I Patel
(74) *Attorney, Agent, or Firm* — Mueting Raasch Group

(57) ABSTRACT

A filament wrapping and reflow system and a method therefrom. The method including wrapping a filament around an elongate substrate along a longitudinal direction between a proximal end of the elongate substrate and a distal end of the elongate substrate. The method also including melting the filament to form at least a portion of the elongate medical device. The system including a substrate system, a filament system, a heater, one or more actuators, and a controller.

20 Claims, 7 Drawing Sheets

(56) References Cited

U.S. PATENT DOCUMENTS

| | | |
|---|---|---|
| 2021/0162176 A1 | 6/2021 | Martin |
| 2021/0290907 A1 | 9/2021 | Martin |
| 2023/0390524 A1 | 12/2023 | Martin |
| 2023/0390525 A1 | 12/2023 | Martin |
| 2023/0390526 A1 | 12/2023 | Martin |

* cited by examiner

FILAMENT WRAPPING AND REFLOW SYSTEM AND METHODS TO MANUFACTURE AN ELONGATE MEDICAL DEVICE

The present application claims the benefit of U.S. Provisional Application No. 62/970,561, filed Feb. 5, 2020, which is incorporated herein by reference in its entirety.

The disclosure generally relates to medical devices and, in particular, additive manufacturing of medical devices, such as catheters and implantable stimulation leads.

A number of medical devices, such as medical catheters, are designed to be navigated through tortuous paths in a human body, such as through a patient's vasculature. Medical catheters and leads are commonly used to access vascular and other locations within a body and to perform various functions at those locations, for example, delivery catheters may be used to deliver medical devices, such as implantable medical leads. Medical catheters and leads may be designed to be sufficiently flexible to move through turns, or curves, in the vasculature yet sufficiently stiff, or resilient, to be pushed through the vasculature. In many cases, such as those involving cardiovascular vessels, the route to the treatment or deployment site may be tortuous and may present conflicting design considerations that may require compromises between dimensions, flexibilities, material selection, operational controls, and the like. These contrasting properties can present challenges in designing and manufacturing catheters.

Existing manufacturing processes, such as existing extrusion techniques, may also limit options in designing and manufacturing catheters. For example, existing extrusion techniques may not allow for precise placement of select components relative to the medical device. Further, it may be difficult to push softer materials unless using a screw extruder or ram extruder.

SUMMARY

The techniques of the present disclosure generally relate to additive manufacturing of medical devices, such as catheters and leads, that allows for the use of a wider range of filament materials to create a wide range of resulting catheter or lead characteristics. For example, a wider range of various properties (e.g., hardness, elasticity, flexural modulus, etc.) can be achieved compared to existing techniques to produce catheters, catheter components, or implantable devices. In particular, the present techniques allow for wrapping filaments at a range of material application rates from, e.g., low speeds (e.g., for fine fibers) to high speeds (e.g., for wider ribbons) during the additive manufacturing, or three-dimensional (3D) printing. Additionally, the present techniques may facilitate new catheters and implantable devices.

An illustrative method of manufacturing an elongate medical device may include wrapping a filament around an elongate substrate along a longitudinal direction between a proximal end of the elongate substrate and a distal end of the elongate substrate and melting the filament to form at least a portion of the elongate medical device.

In one or more embodiments, the filament may include a polymer material.

In one or more embodiments, the filament may include a thermoplastic material, a thermoset polymeric material, or both.

In one or more embodiments, the method may further include covering the filament wrapped around the elongate substrate with a tube prior to melting the filament and removing the tube after melting the filament.

In one or more embodiments, wrapping the filament around the elongate substrate may include wrapping the filament more than one turn around the elongate substrate.

In one or more embodiments, wrapping the filament around the elongate substrate may include wrapping the filament to include slack in one or more turns of the filament.

In one or more embodiments, the method may further include wrapping an additional filament around the elongate substrate between the proximal end and the distal end.

In one or more embodiments, wrapping the additional filament around the elongate substrate may include wrapping the filament to include slack in one or more turns of the additional filament.

In one or more embodiments, the method may further include melting the additional filament to form at least a portion of the elongate medical device.

In one or more embodiments, the additional filament may include one or more of the following: a metal conductor, a polymeric conductor, or an aramid fiber.

In one or more embodiments, wrapping the filament and the additional filament around the elongate substrate may include positioning the filament and the additional filament adjacent one another and wrapping both the filament and the additional filament together between the proximal end and the distal end.

In one or more embodiments, wrapping the additional filament around the elongate substrate may include wrapping the additional filament around the filament after wrapping the filament around the elongate substrate.

In one or more embodiments, wrapping the filament around the elongate substrate may include wrapping the filament at variable pitches along the longitudinal direction, wrapping the additional filament around the elongate substrate at variable pitches along the longitudinal direction, or both.

In one or more embodiments, wrapping the filament around the elongate substrate may include wrapping the filament around the elongate substrate at a decreasing variable pitch from the proximal end to the distal end. Also, wrapping the additional filament around the elongate substrate may include wrapping the additional filament around the elongate substrate at an increasing variable pitch from the proximal end to the distal end.

In one or more embodiments, the filament and the additional filament may be wrapped around the elongate substrate at different pitches.

In one or more embodiments, wrapping the filament around the elongate substrate may include wrapping the filament at variable pitches along the longitudinal direction.

In one or more embodiments, wrapping the filament around the elongate substrate may include one or more of the following: braiding, weaving, or knitting the filament around the elongate substrate.

In one or more embodiments, the method may further include attaching the filament to the elongate substrate at the proximal end of the elongate substrate prior to wrapping the filament.

In one or more embodiments, attaching the filament to the elongate substrate may include melting the filament to the proximal end of the elongate substrate.

In one or more embodiments, attaching the filament to the elongate substrate may include adhering the filament to the proximal end of the elongate substrate.

In one or more embodiments, the method may further include pre-wrapping the filament around the elongate substrate at the proximal end of the elongate substrate such that the at least a portion of the filament is wrapped around another portion of the filament to secure the filament to the proximal end of the elongate substrate.

In one or more embodiments, the method may further include clamping the filament to the proximal end of the elongate substrate prior to wrapping the filament.

In one or more embodiments, the method may further include selectively adding at least one discrete marker to the filament along the longitudinal direction.

In one or more embodiments, the at least one discrete marker may include a visual indicator or a fluoroscopic indicator.

In one or more embodiments, the method may further include selectively adding at least one component to the elongate substrate prior to wrapping the filament around the elongate substrate. Also, wrapping the filament around the elongate substrate may secure the at least one component to the elongate substrate.

In one or more embodiments, the at least one component may include one or more of the following: an electrode, a marker, a balloon, a connector ring or other electrical contact, or a lumen.

In one or more embodiments, the method may further include chemically processing the filament before wrapping the filament around the elongate substrate, chemically processing the filament after wrapping the filament around the elongate substrate, or both.

In one or more embodiments, chemically processing the filament may include one or more of the following: cross-linking a thermoset polymer material with heat, coating with a fluid, or curing using light to initiate a reaction.

In one or more embodiments, the filament may include a cross-sectional shape, which may define a rounded, rectangular, or square shape.

An illustrate additive manufacturing system may include a substrate system, a filament system, a heater, one or more actuators, and a controller. The substrate system may include a clamp to secure an end portion of an elongate substrate extending along a longitudinal direction. The filament system may include one or more spools configured to store one or more filaments. The heater may be configured to deliver heat to any of the one or more filaments disposed on the elongate substrate. The one or more actuators may position the one or more filaments relative to the elongate substrate and may position the heater relative to any of the one or more filaments disposed on the elongate substrate. The controller may be operably coupled to the heater and the one or more actuators. The controller may be configured to control the one or more actuators to wrap the one or more filaments around the elongate substrate secured by the substrate system and activate the heater to deliver heat to at least one of the one or more filaments disposed on the elongate substrate to melt the at least one of the one or more filaments.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
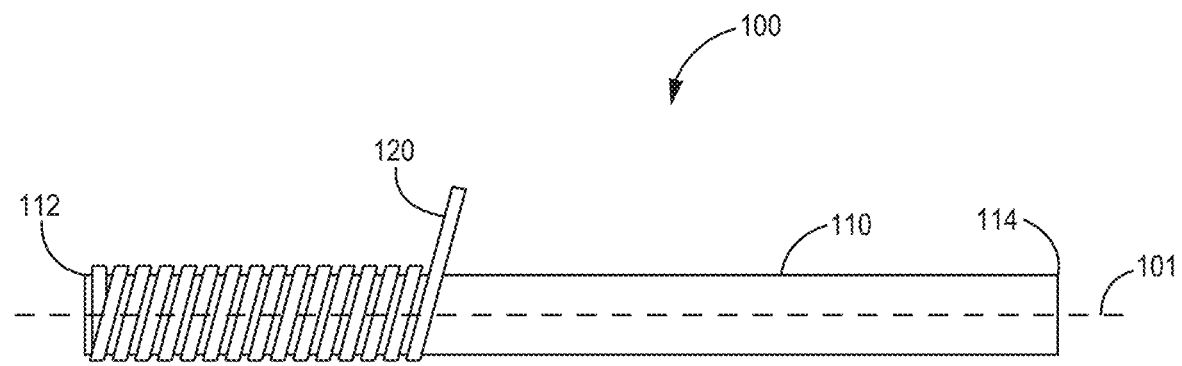
FIG. 1 is a diagram that illustrates a side view of a filament being wrapped on an elongate substrate according to the present disclosure.

The present disclosure generally provides additive manufacturing systems and methods for medical devices, such as catheters and leads, that allows for the use of a wider range of filament materials to create a wide range of resulting catheter or lead characteristics. For example, a wider variety of hardness levels can be achieved compared to existing techniques to produce catheters, catheter components, or implantable devices. Additive manufacturing may also be described as three-dimensional (3D) printing. The additive manufacturing systems of the present disclosure allow feeding filaments at a range of material application rates from low speeds (e.g., low RPM) to high speeds (e.g., high RPM), which may facilitate a wider range of operating conditions for prototyping or manufacturing. For example, in some embodiments, the additive manufacturing systems may allow for feeding filaments at speeds of greater than 2,000 RPM. The application rates may be achieved using various different techniques, for example, the system including multiple payoffs (e.g., spools), multiple strands wound onto individual bobbins, or multiple filament dispense systems. In one or more embodiments, the material application rates may be quantified using volume or mass per time (e.g., $in^3$/sec, g/sec). Further, new catheters and implantable devices may be facilitated by the wider range filament materials and operating conditions. The present techniques may also not be limited to concurrent melting and positioning processes as with existing extrusion techniques.

The systems and methods described herein allow for 3D printing of medical devices, which may facilitate constructions with unique combinations of properties which may enable new treatments. Unique catheter handling properties may be achieved by combining materials in ways not traditionally combined in catheter manufacturing and may include materials that are new to catheter construction. In addition, 3D printing may allow for including other accessories, such as steering capability via pull wires, in a space efficient manner.

For example, the systems, devices, and methods described herein include wrapping filaments around a cylindrical, elongate substrate to form or "build-up" tubular or elongate medical devices (e.g., delivery catheters, stimulation leads, etc.). As such, catheters, leads, and/or other medical devices may be customized when using filament wrapping by adding features along the length of the device in one setup. Specifically, an added feature may be anchored within the device by controlling the tension and, for example, the associated compressive forces, during filament wrapping to bind the feature to the device.

In some embodiments, the system and methods may include elements to modify the filament wrap after the feature is added by thermal or chemical processing to change the state or form. For example, some processes may include melting, crosslinking, coating, or curing to initiate a thermal or chemical reaction to form the filament into the medical device. Further, the medical device may be modified by cutting, clamping, crimping, or holding tools.

Additionally, in some embodiments, the filaments used to wrap and form the medical devices may be selected from various materials to define desired properties of the device. For example, the filament may define a specific hardness that is selected for a specific device application. Further, the filaments may be configured on the medical device to adjust various properties of the medical device. For example, the filaments may be arranged on the medical device in such a way to vary properties for a specific location along the device. Specifically, the filaments may be wrapped with different pitches or density to produce varying properties of the medical device. Similarly, the thickness or cross-sectional shape of a particular filament may contribute to the properties resulting from wrapping that particular filament for the medical device.

In one or more embodiments, multiple filaments may be utilized to increase customizability when manufacturing the devices. For example, two filaments having different hardness values may be combined in different ways (e.g., differing pitches, densities, thicknesses, cross-sectional shape, etc.) to create various properties depending on the ratio or combination of the filaments.

In general, precision placement of filament wraps around an elongate substrate and along a longitudinal axis may facilitate anchoring or creating particular features for a medical device, such as forming layers, securing electrodes or fluid lumens, and adding contrasting markers for visualization. Controlling the filament tension may be used to manage the compressive and axial stresses of the medical device. Further, creating precise transitions from one material to another may facilitate variable properties along the length of the medical device, for example, when using a softer thermoplastic material for a distal end and a harder material for the proximal end.

In some embodiments, components may be anchored to the substrate by wrapping filaments to capture such components. In particular, wrapping under tension may create a compressive force to bind items to the substrate. In contrast, loose wrapping under zero tension may also be used. With filament wrapping, tubular elements may not need to be slid axially along the substrate to secure components to the elongate substrate. This may allow for securing irregularly shaped components, varying diameter components, and even protruding components to be placed against the elongate substrate and secured, or coated, by wrapping.

Techniques of the present disclosure may allow for the construction of new medical devices, such as new catheters, leads, and other tubular medical devices. In addition, more features may be incorporated into a given size device, which may facilitate more therapies with the medical device. In one example, a quadripolar left ventricular (LV) lead may be built using the techniques described herein in a manner that facilitates ease of manufacturing.

As used herein, the term "or" refers to an inclusive definition, for example, to mean "and/or" unless its context of usage clearly dictates otherwise. The term "and/or" refers to one or all of the listed elements or a combination of at least two of the listed elements.

As used herein, the phrases "at least one of" and "one or more of" followed by a list of elements refers to one or more of any of the elements listed or any combination of one or more of the elements listed.

As used herein, the terms "coupled" or "connected" refer to at least two elements being attached to each other either directly or indirectly. An indirect coupling may include one or more other elements between the at least two elements being attached. Either term may be modified by "operatively" and "operably," which may be used interchangeably, to describe that the coupling or connection is configured to allow the components to interact to carry out described or otherwise known functionality. For example, a controller may be operably coupled to a resistive heating element to allow the controller to provide an electrical current to the heating element.

As used herein, any term related to position or orientation, such as "proximal," "distal," "end," "outer," "inner," and the like, refers to a relative position and does not limit the absolute orientation of an embodiment unless its context of usage clearly dictates otherwise.

All scientific and technical terms used herein have meanings commonly used in the art unless otherwise specified. The definitions provided herein are to facilitate understanding of certain terms used frequently herein and are not meant to limit the scope of the present disclosure.

Reference will now be made to the drawings, which depict one or more aspects described in this disclosure. However, it will be understood that other aspects not depicted in the drawings fall within the scope of this disclosure. Like numbers used in the figures refer to like components, steps, and the like. However, it will be understood that the use of a reference character to refer to an element in a given figure is not intended to limit the element in another figure labeled with the same reference character. In addition, the use of different reference characters to refer to elements in different figures is not intended to indicate that the differently referenced elements cannot be the same or similar.

FIG. 1 shows one example of a filament 120 wrapping around an elongate substrate 110 (e.g., a mandrel). The elongate substrate 110 extends along a longitudinal direction 101 between a proximal end 112 and a distal end 114. It is noted that the longitudinal direction 101 may extend along a path that is curved in two or three dimensions (e.g., to form a medical device 100 following the same path) but is shown as extending along a straight longitudinal axis in FIGS. 1-4. Additionally, in one or more embodiments, the medical device 100 may be curved after being formed. Further, the elongate substrate 110 may define any suitable shape and size. The elongate substrate 110 may be described as forming the basis around which the filament 120 is wrapped and melted/cured to create the medical device 100. In some embodiments, the medical device 100 may be a component, part, subassembly or a single layer element that may be added to other components.

The elongate substrate 110 may include any suitable components in forming the desired medical device 100. For example, the elongate substrate 110 may fixture or hold components in "nests" to securely wrap the filament 120 around (e.g., a breakaway tab on the components may allow for the elongate substrate 110 to be easily removed during/after the manufacturing process). Specifically, the elongate substrate 110 may hold conductors (e.g., in grooves on the elongate substrate 110 surface), which remain in the medical device 110 (e.g., within the cured/melted filament 120) when the elongate substrate 110 is removed. In one or more embodiments, the elongate substrate 110 may be a mandrel that is removed from within the filament 120 after melting/curing to define a lumen extending through the melted/cured filament 120 (e.g., forming a catheter). Also, in one or more embodiments, the elongate substrate 110 may include other components, conductive materials, markers (as discussed herein) to fuse with filament 120 when melted/cured (e.g., forming a lead).

Figure 2:
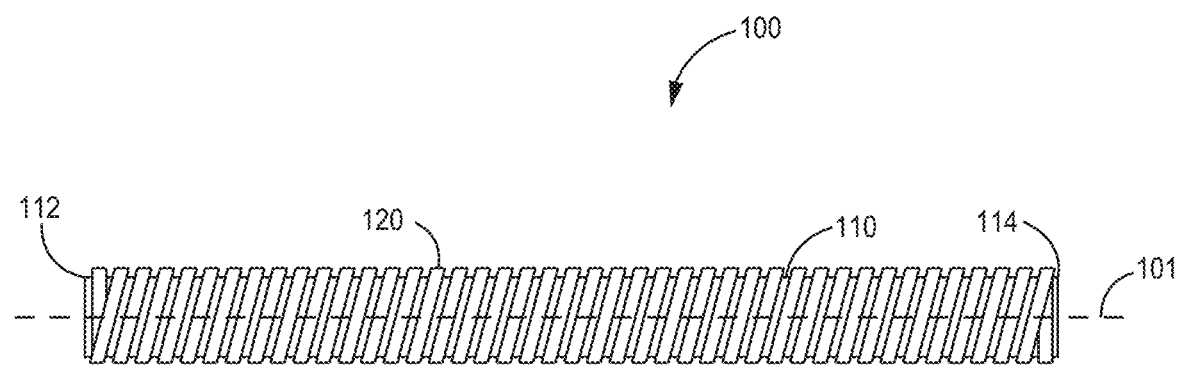
FIG. 2 is a diagram that illustrates a side view of a filament wrapped on an elongate substrate between a proximal end of the elongate substrate and a distal end of the elongate substrate.

As shown in FIG. 1, the filament 120 may be wrapped around the elongate substrate 110 starting at the proximal end 112 of the elongate substrate 110 and extending towards the distal end 114 of the elongate substrate 110. In one or more embodiments, the filament 120 may be wrapped around only a portion of the elongate substrate 110 (e.g., proximate the proximal end 112, between the proximal and distal ends 112, 114, proximate the distal end 114). Further, the filament 120 may be wrapped around the elongate substrate 110 in one or more sections around the elongate substrate 110. For example, a first section of the filament 120 may wrap around the elongate substrate 110 for a length of the elongate substrate 110 that is adjacent to a length of the elongate substrate 110 having no filament 120 wrapped around, which may be followed by another length in which a second section of the filament 120 is wrapped around the elongate substrate 110. Further yet, the filament 120 may wrap around the elongate substrate 110 for the entire length of the elongate substrate 110 (e.g., contiguous between the proximal and distal ends 112, 114), e.g., as shown in FIG. 2.

The filament 120 may include any suitable material. For example, in one or more embodiments, the filament 120 may include a polymer material. Specifically, the filament may include a thermoplastic material, a thermoset polymeric material, a thermoplastic elastomer, nylon, a thermoplastic polyurethane (TPU), thermosets silicone, polyethylene terephthalate (PET), polybutylene terephthalate (PBT), polyisobutylene (PIB), etc., or combinations thereof. As will be described further herein, in one or more embodiments, the filament 120 may include other components such as, for example, one or more metal conductors, one or more polymeric conductors, one or more aramid fibers, or combinations thereof. Further, the filament 120 may define any suitable cross-sectional shape such as, e.g., rounded, rectangular, square, teardrop-shaped, triangular, etc. In one or more embodiments, the filament 120 may define lobes that may form a helix that may allow rotation to create some axial forces including, e.g., a crescent moon cross-sectional shape to allow the filament 120 to wrap around the elongate substrate 110, another filament, one or more other components, lobe on a camshaft, helical splines, etc.

In some embodiments, a metal conductor may be wrapped around the elongate substrate 110 and include an electrode on the surface of the elongate medical device 100. Further, the filament 120 may be used to fill the void space between individual turns of the metal conductor. In some embodiments, a polymer filament 120 may also be laid down immediately before one or more metal conductors. Further, in some embodiments, the filament 120 may be laid down simultaneously with the metal conductors. The metal conductors may be single filar metal conductors or multi-filar metal conductors. In some embodiments, the filament 120 may be wrapped to maintain a controlled exposed surface area of the one or more metal conductors and electrodes. Such control of exposed surface area may be used, for example, in the connector of an implantable stimulation lead, which may be used in addition, or as an alternative, to a machined ring connector. Further, a conductive polymer filament may be wrapped prior to (under), during, or after (over) the coil electrode coiling formed by one or more metal conductors. The conductive polymer filament (e.g., flexible electrode) may include (e.g., be made of) any suitable material, such as a poly(3,4-ethylene dioxythiophene) (PEDOT) or carbon black loaded in polyurethane (e.g., a conductive polymer including Lubrizol Pellethane 2363-75D (Shore D 75) thermoplastic polyurethane doped with 20% carbon black).

The filament 120 may wrap around the elongate substrate 110 in various different ways. For example, the filament 120 wrapping around the elongate substrate 110 may be defined as more than one complete turn or spin (e.g., extending 360 degrees) around the elongate substrate 110. Specifically, as shown in FIG. 2, the filament 120 wraps around the elongate substrate 110 with multiple turns between the proximal and distal ends 112, 114. However, in one or more embodiments, the filament 120 wrapping around the elongate substrate 110 may be defined as extending less than a full rotation around the elongate substrate 110 (e.g., extending a half-turn, extending parallel to the longitudinal direction, etc.). Furthermore, in one or more embodiments, the filament 120 may be wrapped around the elongate substrate 110 by braiding, weaving, knitting, etc. the filament 120 around the elongate substrate 110.

Figure 4:
FIG. 4 is a diagram that illustrates the wrapped elongate substrate of FIG. 2 after the filament disposed thereon is melted.

After the filament 120 is wrapped around the elongate substrate 110 (e.g., along at least a portion thereof), the filament 120 may be melted or cured to form at least a portion of the medical device 100 as shown in FIG. 4. In other words, the melting or curing the filament 120 may convert the filament 120 from a distinct thread of material to a continuous material along the longitudinal axis 101 (e.g., melting/curing the filament 120 to bridge the gaps between coiled strands of the filament 120). For example, the filament 120 may be flowed or "squished" sideways during the melting/curing process to connect adjacent filaments.

In addition to forming at least a portion of the medical device 100, the melted/cured filament 120 may adhere, bond, stabilize, and/or join other components within the medical device 100 (e.g., disposed within the filament 120, elongate substrate 110, or therebetween). The wrapped and melted filament 120 may bond the filament to itself and to the elongate substrate 110. Trapped air may also be forced out of the construction (e.g., between strands of the filament 120) and may increase the density of the filament or other components on the elongate substrate 110.

In one or more embodiments, the melting/curing of the filament 120 may include thermally or chemically processing the filament 120 before wrapping the filament 120 around the elongate substrate 110, thermally or chemically processing the filament 120 after wrapping the filament 120 around the elongate substrate 110, or both. Specifically, the thermal processing may include heating the filament 120 and the chemical processing may include cross-linking a thermoset polymer material (of the filament 120) with heat, coating the filament 120 with a fluid (e.g., to increase lubricity, modify the surface underneath for better adhesion, ink for marker/text/image, etc.), curing the filament 120 using light to initiate a reaction (e.g., using different wavelengths of light to initiate cross-linking reaction in polymer blends, depolymerize others, or make foam by releasing gases as a reaction product), etc.

Figure 3:
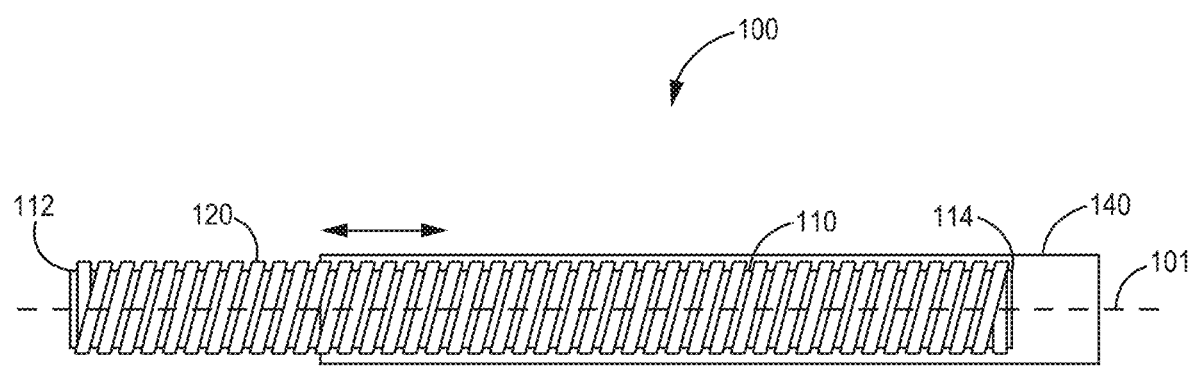
FIG. 3 is a diagram that illustrates the wrapped elongate substrate of FIG. 2 including a tube extending thereover.

In one or more embodiments, prior to melting/curing the filament 120 that is wrapped around the elongate substrate 110, the filament 120 may be covered with a tube 140, e.g., as shown in FIG. 3. The tube 140 may be sized to extend over an outer surface of the wrapped filament 120 and may be formed of any suitable material. In some embodiments, the tube 140 may be provided in a tubular form. In other embodiments, the tube 140 may be provided in ribbon form or sheet form. For example, a tube in sheet form may be configured to shrink primarily in a radially inward direction.

The tube 140 may be configured to move along the longitudinal direction 101 to slide over the filament 120 wrapped elongate substrate 110. Once the tube 140 is positioned over a portion or the entire elongate substrate, the filament 120 may be melted/cured. The tube 140 may assist in containing and controlling the flow of material from the filament 120 during melting/curing. For example, in one or more embodiments, the tube 140 may assist in shaping the melted/cured material of the filament 120, which shapes the at least a portion of the medical device 100. After the filament 120 is melted/cured, the tube 140 may be removed from the medical device 100 or left behind. The tube 140 may include (e.g., be made of) any suitable material (e.g., a material that is prevented from melting/curing by the same process as the filament 120).

In some embodiments, the tube 140 may be described as a heat shrinkable tube. The tube 140 may shrink primarily circumferentially and may provide mostly radially compressive forces to the filament 120 and to other components on the elongate substrate 110.

In some embodiments, the filament 120, the elongate substrate 110, the tube 140, and any other components on the substrate 110 contained by the tube 140 may be passed through a heated orifice (e.g., heater 230 described further herein) over the wrapped layer that is slightly smaller in inner diameter (ID) than the outer diameter (OD) of the tube 140. Such an arrangement may facilitate applying forces to bond melted material and to force out trapped air. In some embodiments in which a tube 140 is not used, a heated orifice may be passed along the surface of the filaments 120 to provide head for melting/curing and also constrain the OD. The heated orifice may be slid on from one end or split to allow the heated orifice to be closed around the filament 120/elongate substrate 110. Further, the heated orifice may be drawn along the longitudinal axis 101, or just positioned, heated, cooled, and removed (e.g., to melt/cure a particular location).

Furthermore, various characteristics may be attributed to techniques and configurations of wrapping the filament 120 around the elongate substrate 110. For example, the pitch of the filament 120, the density of wrapping, and the tension applied to the filament 120 while wrapping may all contribute to the properties of the material after the filament 120 is melted/cured and formed into at least a portion of the medical device 100.

In one or more embodiments, the filament 120 may be wrapped around the elongate substrate 110 while maintaining a controlled tension on the filament 120. Controlling the tension applied to the filament 120 while wrapping around the elongate substrate 110 may assist in placing the filament 120 and applying forces to components between the filament 120 and the elongate substrate 110. Specifically, for example, the filament 120 may be wrapped around the elongate substrate 110 to include slack portions or loose wrapping (e.g., under low or zero tension) in, e.g., one or more turns. In one or more embodiments, the slack portions or loose wrappings may be defined by directional changes. Also, for example, the filament 120 may be wrapped around the elongate substrate 110 to be taut or under high tension. Further, the tension on the filament 120 may be something therebetween. It is noted that different tensions and tensioning methods may be used based on the type of material.

In some embodiments, the tension may correspond to a type of material. For example, a copper filament may be wrapped using low or zero tension. In another example, a steel filament may be wrapped using high tension.

In some embodiments, to create slack, a tensioner associated with the filament 120 may go to a zero condition without backlash. Rotation of the elongate substrate may be reversed in some cases. In some embodiments, a point of already laid down filament 120 may be fixed, then a controlled slack may be obtained using the tensioner going to the zero condition.

A slack portion may be particularly beneficial when wrapping a metal conductor material because torque on the medical device 100 during use may apply torque on the metal conductor material. If the metal conductor material is taut or under high tension, it may be more prone to fracturing. However, if the metal conductor material is loose or including slack portions, the metal conductor material may have the flexibility to twist without risking breaking or fracture. For example, if a composite thermoplastic shaft including a metal braid is created, separate conductors may be added to the outside of the shaft and include some degree of slack such that when the catheter is bent, the conductors may not experience high axial forces when positioned farther from the neutral axis of the composite.

Additionally, in one or more embodiments, tension from filament wrapping may induce compressive stress into the finished assembly. For example, if the filament 120 is wrapped/braided/coiled with too much filament tension, the assembly may shrink tightly onto the elongate substrate 110, which may prevent the elongate substrate 110 from being removed from the wrapped filament 120. Further, in some embodiments, higher filament tension may be helpful to laminate, secure features, or close off a lumen being constructed in the creation of the medial device 100. Also, if the residual stresses of the filament 120 are not controlled, the medical device 100 may have differing axial length in the finished device during post-forming (e.g., sterilization, storage, shipment, etc.).

In one or more embodiments, the pitch (e.g., angle) and density of the filament 120 wrapped around the elongate substrate 110 may be altered as desired to, e.g., control the amount of material at a specific location. The pitch and density of the filament 120 wrapped around the elongate substrate 110 may also be described by the proximity or gap between each adjacent turn of the filament 120. For example, a filament 120 wrapped with a low pitch may result in subsequent filament portions being closer together (e.g., smaller gap therebetween) as compared to a filament 120 wrapped with a high pitch (e.g., the filament portions may be farther apart and have a larger gap therebetween). Specifically, the filament 120 may wrapped around the elongate substrate 110 in a range between "open" (e.g., space or air between adjacent filaments/fibers), "closed" (e.g., no space between adjacent filaments/fibers or "solid"), "overlapping," or anywhere therebetween. The proximity of filament portions relative to one another (e.g., pitch or density) may affect the amount of material present within a specific region. Therefore, the pitch or density may affect the material properties of the filament 120 wrapped in that specific region. In one or more embodiments, it may be desirable to leave gaps between adjacent filaments/fibers (e.g., less than a solid density) to, e.g., create cavities that are more echogenic on ultrasound or layers that can slip or stretch when the medical device 100 is flexed.

Figure 7:
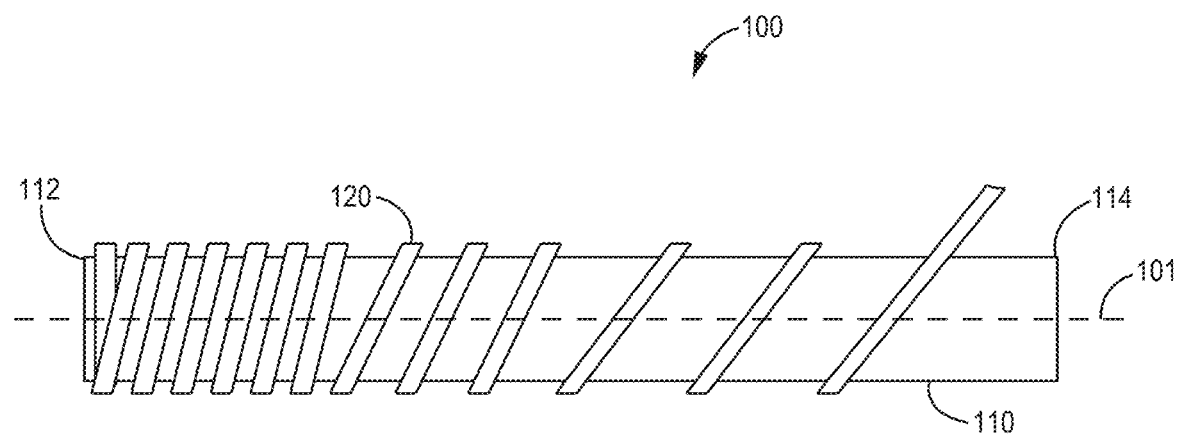
FIG. 7 is a diagram that illustrates a side view of an illustrative medical device having filament wrapped around an elongate substrate at different pitches.

The filament 120 may define a constant pitch, a variable pitch, or combinations thereof. For example, as shown in FIG. 2, the filament 120 defines a constant pitch along the longitudinal direction 101 from the proximal end 112 to the distal end 114. In other embodiments, the filament 120 may define variable pitches along the longitudinal direction 101 from the proximal end 112 to the distal end 114, e.g., as shown in FIG. 7.

Figure 6A:
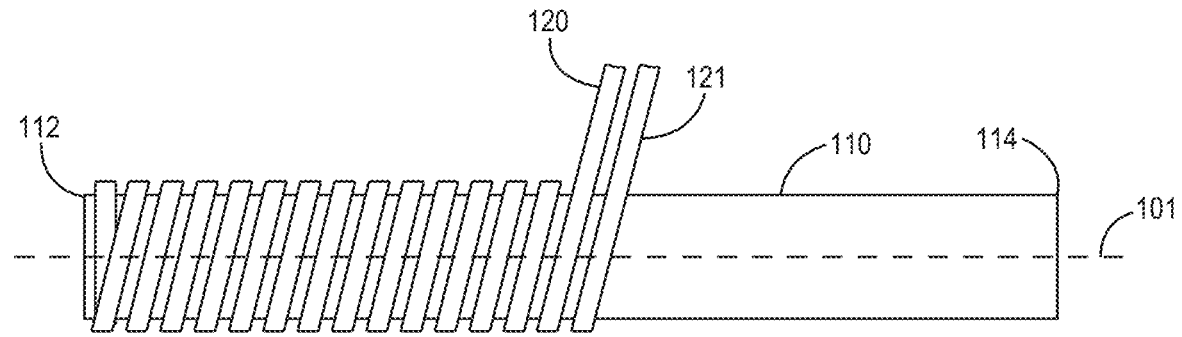
FIG. 6A is a diagram that illustrates a side view of an illustrative medical device having two proximate filaments wrapped around an elongate substrate.
Figure 6B:
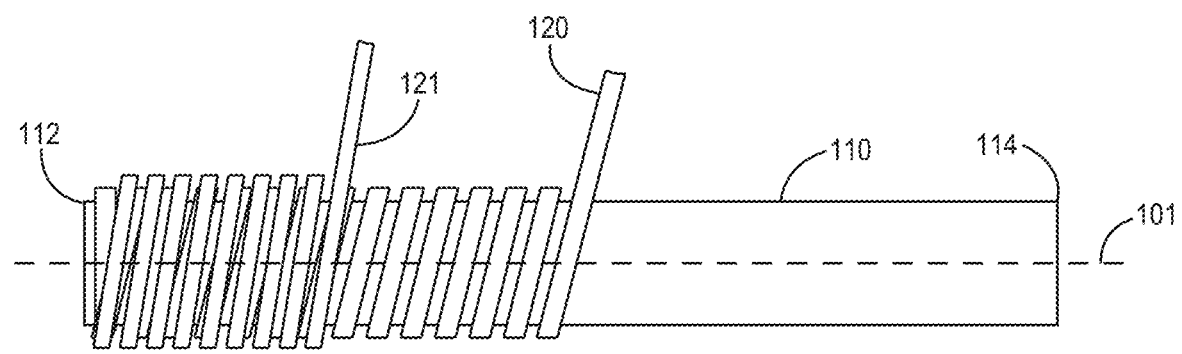
FIG. 6B is a diagram that illustrates a side view of an illustrate medical device having a first filament wrapped around an elongate substrate and a second filament wrapped around the first filament.

In one or more embodiments, the medical device 100 may include an additional filament 121 wrapped around the elongate substrate 110 (e.g., in addition to the filament 120), as shown in FIGS. 6A and 6B. It is noted that the additional filament 121 may include any characteristic or configuration similar to as described herein pertaining to filament 120. The additional filament 121 may be wrapped around the elongate substrate 110 at any location between the proximal end 112 of the elongate substrate 110 and the distal end 114 of the elongate substrate 110. For example, the additional filament 121 may wrap around the elongate substrate 110 along the longitudinal direction 101 from the proximal end 112 to the distal end 114 (e.g., similar to the filament 120 shown in FIG. 2). Also, for example, the additional filament 121 may wrap around the elongate substrate 110 for only a portion of the elongate substrate 110 along the longitudinal direction 101 (e.g., proximate the proximal end 112, proximate the distal end 114, or anywhere therebetween). Further, for example, the additional filament 121 may wrap around the elongate substrate in sections such that the additional filament 121 is wrapped for a portion of the longitudinal direction 101 followed by a portion that is not wrapped by the additional filament 121.

The additional filament 121 may be wrapped in any suitable way relative to the filament 120 around the elongate substrate 110. For example, the filament 120 and the additional filament 121 may be wrapped around the elongate substrate 110 by positioning the filament 120 and the additional filament 121 adjacent or proximate one another and wrapping the pair together between the proximal end 112 and the distal end 114 (e.g., for any length along the longitudinal direction 101), e.g., as shown in FIG. 6A. In other words, the filament 120 and additional filament 121 may alternate along the longitudinal direction 101 and have the exact same pitch (e.g., because the filament 120 and additional filament 121 are wrapped side-by-side). In such embodiment, the filament 120 and the additional filament 121 may or may not be in contact with one another along the longitudinal direction 101.

Also, for example, the filament 120 may be wrapped around the elongate substrate 110 and the additional filament 121 may be wrapped around the filament 120 thereafter, as shown in FIG. 6B. In other words, the additional filament 121 may be wrapped around the filament 120 after the filament 120 is wrapped around the elongate substrate 110 (e.g., to overlap the filament 120). In such embodiment, the filament 120 and the additional filament 121 may or may not have the same pitch.

While a first filament (e.g., filament 120) and a second filament (e.g., additional filament 121) are specifically described herein, any number of filaments may be wrapped around the elongate substrate 110 to form the medical device 100. The filaments may be wrapped relative to each other in any suitable way. For example, the filaments may be wrapped by coiling, braiding, weaving, knitting, etc. Furthermore, in one or more embodiments, multiple filaments may be wrapped using opposite helices (Left Hand/Right Hand) or the same directional helix. Also, in one or more embodiments, a single filament may be wrapped in a first direction along the longitudinal direction 101 and then wrapped back over itself in a second direction that is opposite the first direction (e.g., the filament may wrap back and forth multiple times in some embodiments). Further, multiple filaments may be added together or sequentially. In one or more embodiments, a first filament may be wrapped around the elongate substrate 110 and then paused while a second filament is wrapped around the elongate substrate 110. Thereafter, wrapping of the first filament may be continued or restarted.

Further, the additional filament 121 may also be melted to form at least a portion of the medical device 100 (e.g., if the additional filament 121 is a polymer material). As such, the filament 120 and the additional filament 121 may combine during the melting/curing such that the resulting material defines properties and characteristics different from the individual components. For example, the hardness of each material (e.g., measured by Shore durometer) may combine to form a material having a separate hardness. Further, changing the ratio of the amount of the filament 120 combined with the amount of the additional filament 121 (e.g., assuming each has a different hardness), changes the resulting hardness. Therefore, by altering the pitch and/or density of either of the filament 120 and the additional filament 121, a resulting material (e.g., after melting/curing) having a desired hardness may be produced.

For example, in one or more embodiments, the filament 120 may be wrapped around the elongate substrate 110 at variable pitches along the longitudinal direction 101, the additional filament 121 may be wrapped around the elongate substrate 110 at variable pitches along the longitudinal direction 101, or both. Specifically, in one or more embodiments, the filament 120 may be wrapped around the elongate substrate 110 at a decreasing variable pitch from the proximal end 112 to the distal end 114 and the additional filament 121 may be wrapped around the elongate substrate 110 at an increasing variable pitch from the proximal end 112 to the distal end 114 (e.g., FIG. 7 illustrates the filament 120 wrapped around the elongate substrate 110 at an increasing variable pitch from the proximal end 112 to the distal end 114). To wrap the filament 120 and the additional filament 121 at varying pitches, the filament 120 and the additional filament 121 may be wrapped over the other (e.g., such that one overlaps the other).

Therefore, in one or more embodiments, there may be more material from the filament 120 proximate the proximal end 112 (as compared to the distal end 114) and more material from the additional filament 121 proximate the distal end 114 (as compared to the proximal end 112). As such, the resulting material after melting/curing may have a larger ratio of filament 120 to additional filament 121 proximate the proximal end 112 and a larger ratio of additional filament 121 to filament 120 proximate the distal end 114. In such configuration, if the filament 120 defines a greater Shore durometer hardness than the additional filament 121, the medical device 100 would define a Shore durometer hardness that is larger proximate the proximal end 112 as compared to the distal end 114. Furthermore, in one or more embodiments, the filament 120 and the additional filament 121 may be wrapped around the elongate substrate 110 at different pitches (e.g., at a specific point along the longitudinal direction 101).

One or more filaments, such as the additional filament 121, may be made of a composite material. In one or more embodiments, the additional filament 121 may be or include a polymeric conductor, a metal conductor (such as a pre-insulated metal conductor), an aramid fiber (which may be dipped in adhesive or coating solution prior to wrapping), a coated or insulated material (e.g., a wire or cable), etc. Further, the filament 120 and the additional filament 121 (and any number of other filaments) may be combined for any suitable purpose. For example, two or more filaments may be combined to form a flat ribbon cable made up of two or more individually insulated metal conductors joined side by side (e.g., to form a strip). Also, as described herein, two or more filaments may be configured to melt or cure such that the materials of each are combined to form at least a portion of the medical device 100. Further, for example, the filament 120 may include a material configured to melt/cure and the additional filament 121 may include a material configured to not melt/cure such that when the filament 120 is melted/cured, the material of the additional filament 121 is infused with the filament 120.

Figure 5:
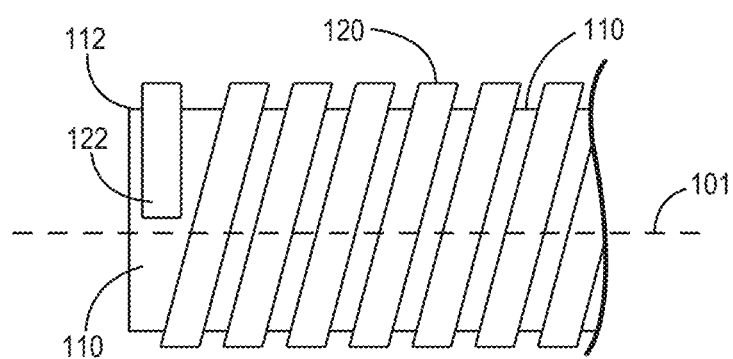
FIG. 5 is a diagram that illustrates an expanded view of another illustrative embodiment of a filament wrapped elongate substrate.

As shown in FIG. 5, a portion (e.g., an end 122) of the filament 120 may be secured or anchored prior to wrapping the filament 120 around the elongate substrate 110. For example, the filament 120 may be prevented from moving relative to the elongate substrate 110 when the filament 120 is pulled or wrapped around the elongate substrate 110. Specifically, the filament 120 may be attached to the elongate substrate 110 (e.g., at the proximal end 112 of the elongate substrate 110) prior to wrapping the filament 120. In one or more embodiments, attaching the filament 120 to the elongate substrate 110 may include melting or adhering the filament 120 (e.g., proximate to the end 122 of the filament 120) to the proximal end 112 of the elongate substrate 110.

Also, in one or more embodiments, the filament 120 may be "pre-wrapped" (e.g., prior to wrapping) around the elongate substrate 110 (e.g., at the proximal end 112 of the elongate substrate 110) such that the at least a portion of the filament 120 may be wrapped around another portion (e.g., proximate to the end 122 of the filament 120) of the filament 120 to secure the filament 120 to the elongate substrate 110 (e.g., the proximal end 112). For example, as shown in FIG. 1, a portion of the filament 120 (e.g., proximate to the proximal end 112) is positioned between the elongate substrate 110 and another portion of the filament 120 such that the another portion of the filament 120 may apply a pressure (e.g., towards the elongate substrate 110) on the portion of the filament 120. Further, in one or more embodiments, the filament 120 may be clamped (e.g., using a clamp) to the elongate substrate 110 (e.g., proximate to the proximal end 112) prior to wrapping the filament 120 around the elongate substrate 110.

Figure 8:
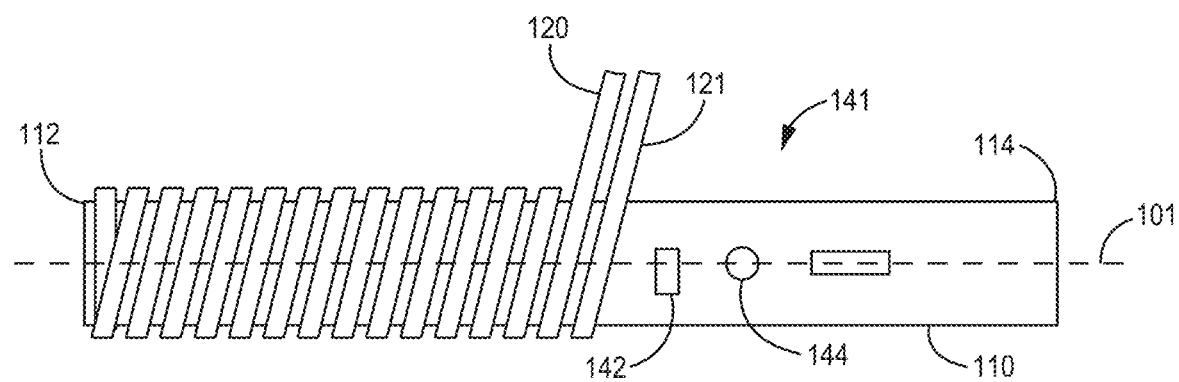
FIG. 8 is a diagram that illustrates a side view of an illustrative medical device having one or more components to be wrapped by one or more filaments.

In one or more embodiments, the medical device 100 may include features 141 that may be selectively added to the filament 120. For example, as shown in FIG. 8, the medical device 100 may include at least one discrete marker 142 within or under (e.g., between the filament 120 and the elongate substrate 110) the filament 120 along the longitudinal direction 101. Specifically, the at least one discrete marker 142 may include a visual indicator or a fluoroscopic indicator. More specifically, the fluoroscopic indicator may include a nitinol member, a metal member, or a radiopaque member. In one or more embodiments, the at least one discrete marker 142 may include a thermoplastic polyurethane loaded with platinum powder to create a flexible marker band.

Further, in one or more embodiments, at least one other component 144 may be selectively added to the elongate substrate 110 prior to wrapping the filament 120 around the elongate substrate 110. Wrapping the filament 120 around the elongate substrate 110 may secure the at least one component 144 to the elongate substrate 110 (e.g., by pinning the at least one component 144 between the filament 120 and the elongate substrate 110). Thereafter, the filament 120 may be melted/cured such that the at least one component 144 may be integral with the material from the filament 120. The at least one component may include one or more of an electrode, a marker, a balloon, a connector ring or other electrical contact, a lumen, etc. In one or more embodiments, a conductive polymer filament may terminate into a conductive polymer flexible electrode. For example, if the filament is conductive and the impedance changes with strain, the pitch near termination may be configured to measure tip force. This configuration may be used in RF ablation catheters and atrial delivery systems in both the left and right atria.

Figure 9:
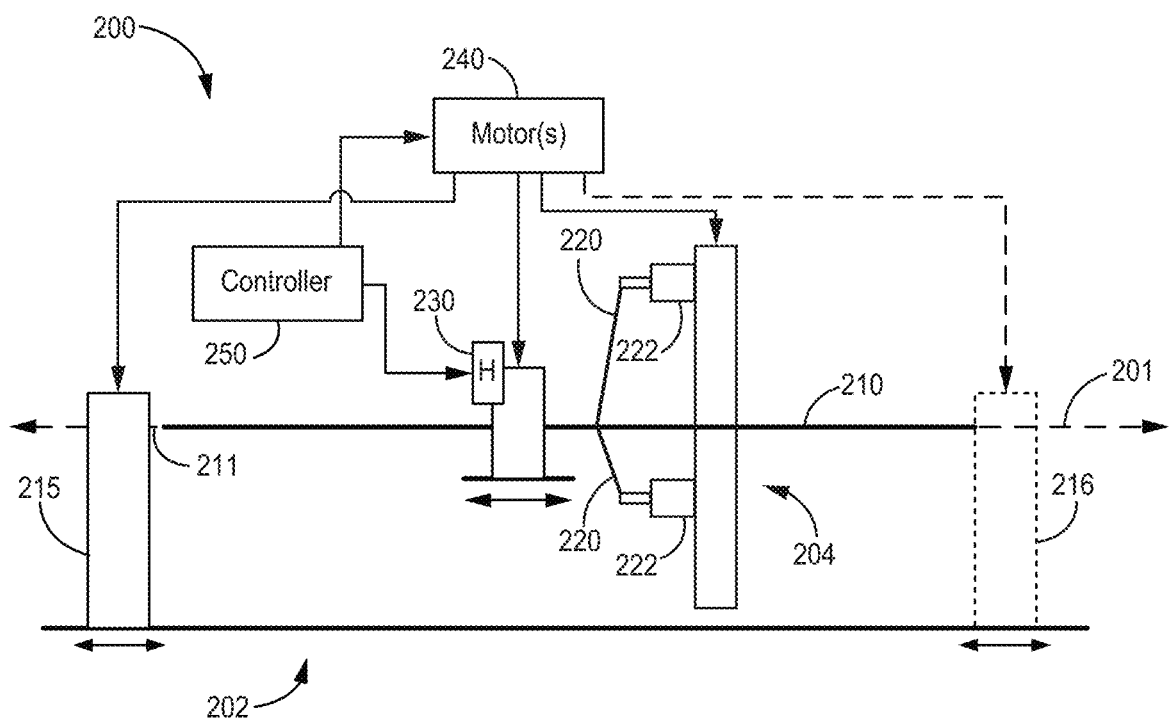
FIG. 9 is a conceptual diagram that illustrates an additive manufacturing system to wrap an elongate substrate with filaments to form a medical device.

An additive manufacturing system 200 for making the medical device 100 is illustrated in FIG. 9. The system 200 may include a substrate system 202 including a clamp 215 (e.g., a head stock) to secure an end portion 211 of an elongate substrate 210 (e.g., a mandrel), which may extend along a longitudinal axis 201. In one or more embodiments, the substrate system 202 may include another clamp 216 (e.g., a tail stock), illustrated in broken lines as optional, to secure the other end portion of the elongate substrate 210. For example, one or both of the head stock 215 and the tail stock 216 may move for a variety of different reasons (e.g., tensioning the elongate substrate 210, positioning different components, etc.). Further, one or both of the head stock 215 and the tail stock 216 may be mounted on an arm (e.g., a robot arm) that moves in multiple dimensions (i.e., not just in a single axial direction).

The system 200 may also include a filament system 204 including one or more spools 222 (e.g., bobbins, spindles, payoff, cylinders, etc.) configured to store one or more filaments 220. For example, the one or more filaments 220 may wrap around the one or more spools 222 and dispense therefrom. The one or more spools 222 may rotate about an axis that allows more of the one or more filaments attached to the spool 222 to be released, or no longer restricted from movement, by the spool 222. The one or more spools 222 may control the speed at which the filament 220 may be dispensed from the spool 222.

In one or more embodiments, the filament system 204 may be positioned on one side of the elongate substrate 210 or on multiple sides of the elongate substrate 210 (e.g., such that the elongate substrate 210 extends through the filament system 204). In such embodiments that the elongate substrate 210 extends through the filament system 204, the filament system 204 may open and close around the elongate substrate 210 to easily remove or position the filament system 204 relative to the elongate substrate 210.

Further, the system 200 may include a heater 230 configured to deliver heat to any of the one or more filaments 220 disposed on the elongate substrate 210. For example, after the one or more filaments 220 are wrapped around the elongate substrate 210, the one or more filaments 220 may be melted/cured by the heater 230. In one or more embodiments, the heater 230 may define a passage through which the elongate substrate 210 extends.

Also, the system 200 may include one or more actuators 240 (e.g., motors, pneumatic cylinders, position control systems, etc.) configured to position the one or more filaments 220 relative to the elongate substrate 210. For example, the one or more actuators 240 may be configured to move the filament system 204 (which includes the one or more filaments 220) along the longitudinal direction 201 so that the one or more filaments 220 may be aligned with the elongate substrate 210. Specifically, as the filament 220 is wrapped around the elongate substrate 210, the filament system 204 may move so that the filament 220 may continue to wrap around the elongate substrate 210 along the length of the longitudinal direction 201. Regardless, the filament system 204 may move relative to the elongate substrate 210 along any path defined by the longitudinal direction 201 such as, e.g., axially or along a curved path. Further, the filament system 204 may move relative to the elongate substrate 210 in a variety of different ways (e.g., the filament system 204 may move relative to a fixed elongate substrate 210, the elongate substrate 210 may move relative to a fixed filament system 204, or both the elongate substrate 210 and the filament system 204 may move).

In order for the filament 220 to be wrapped around the elongate substrate 210, the filament system 204 may also rotate relative to the elongate substrate 210. For example, in one or more embodiments, the filament system 204 may remain stationary while the elongate substrate 210 rotates about the longitudinal direction 201. Specifically, the elongate substrate 210 may rotate based on a connection with the clamp 215 and/or the other clamp 216. For example, the clamp 215 and/or the other clamp 216 may be statically coupled to the elongate substrate 210 such that when the clamp 215 rotates, so too does the elongate substrate 210. In one or more embodiments, the elongate substrate 210 may remain stationary (e.g., relative to the clamp 215) while the filament system rotates relative to the elongate substrate 210.

Further, the one or more actuators 240 may be configured to position the heater 230 relative to any of the one or more filaments 220 disposed on the elongate substrate 210. For example, the heater 230 may move along the longitudinal direction 201 as the one or more filaments 220 are wrapped around the elongate substrate 210. In one or more embodiments, the heater 230 may be positioned on one side of the elongate substrate 210 or on multiple sides of the elongate substrate 210 (e.g., such that the elongate substrate 210 extends through the heater 230). In such embodiments that the elongate substrate 210 extends through the heater 230, the heater 230 may open and close around the elongate substrate 210 to easily remove or position the heater 230 relative to the elongate substrate 210

Specifically, the heater 230 may be positioned a specified distance behind the point at which the filaments 220 wrap around the elongate substrate 210 such that the filaments 220 are melted shortly after being wrapped. In other embodiments, the filaments 220 may be wrapped around all or a large portion of the elongate substrate 210 before the heater 230 passes over the filament 220 to melt the filament 220. As such, the wrapping and melting process may be described as either a one-pass process (e.g., the filament system 204 and the heater 230 moving in connection to one another) or a two-pass process (e.g., the heater 230 moves to heat the filament 220 after the filament 220 is completely wrapped around the elongate substrate 210).

However, whether it is a one-pass or two-pass process, it may be described as a one-setup process. In other words, the elongate substrate 210 may be wrapped with the filament 220 and the filament 220 may be melted by the heater 230 without removing and/or moving (e.g., to a different machine) the elongate substrate 210. For example, some existing processes may require the filament to wrap around the elongate substrate on a first machine and then the elongate substrate is moved to a second machine to melt the filament.

A controller 250 of the system 200 may be operably coupled to the heater 230 and/or the one or more actuators 240. The controller 250 may be configured to control the one or more actuators 240 to wrap the one or more filaments 220 around the elongate substrate 210 secured by the substrate system 202. The controller may also be configured to activate the heater 230 to deliver heat to at least one of the one or more filaments 220 disposed on the elongate substrate 210 to, e.g., melt/cure the at least one of the one or more filaments 220.

In general, the system 200 may be used to produce individual tubular constructions of different materials along the length of a medical device, which may allow precise control of medical device construction, which may allow for construction with or without tubes being slid over ends of the elongate substrate used to form the medical device. In addition, the system 200 may be configured to handle a wide range of material stiffness, such as 10A Shore durometer to very hard polymers and a range of metal wires, either insulated or uninsulated.

In some embodiments, the system 200 may precisely add thermoplastic polymer and metal to create tubular catheter constructions. Materials may be added as exterior layers to an elongate substrate 210 held between the headstock clamp 215 and the tailstock clamp 216 (or cantilevered with only one clamp 215, 216 if an aspect ratio is short enough). A tensioner to control tension between the clamps 215, 216 may be included to facilitate concentricity of components of the medical device.

The system 200 may dispense materials in one or more ways. In some embodiments, the system 200 may include a "pressure coating" crosshead. The crosshead may draw out a layer of thermoplastic out of a polymer-filled annulus by axial/rotational motion between the crosshead and the elongate substrate (e.g., mandrel). A supply of polymer may be provided to the crosshead, for example, using strand-fed pinch rolls (e.g., similar to a fused deposition modeling head), a single-screw or twin-screw extruder, or a ram extruder.

In some embodiments, the system 200 may include a pixel-by-pixel deposition head to provide molten material to the elongate substrate 210 (e.g., similar to flat-bed 3D printing).

In some embodiments, the system 200 may supply wire or polymer filament as continuous strands from a payoff, such as spools 222. The filament may be wrapped around the elongate substrate 210 by relative rotation between the mandrel and the payoffs.

In some embodiments, the system 200 may lay the filament along the elongate substrate 210 in an axial, or longitudinal, manner. Specifically, the filament may extend along the elongate substrate 210 in any different pattern from purely circumferential (e.g., stacking) to axial to zigzag. The pattern of the filaments may be used to integrate operable connections in the medical device such as, e.g., lumens or electrical conductors, or may create visibly distinct patterns for location/positioning or may change the device properties locally.

In some embodiments, the system 200 may apply the filament to the elongate substrate 210 at different angles. The filament may also be applied with slack loops. Such variance in angle and slack may allow the filament to serve more strongly, or less strongly, as a structural element of the medical device when the device is deflected in torsion or tension.

The system 200 may also fuse thermoplastic materials with the addition of heat, for example, using a physical heated clamp touching the materials, laser heating, radiant heating, hot air, or a reflowed heat shrink. In some embodiments, thermoset materials may be cross-linked by the application of heat in a similar manner.

The system 200 may be described as a lathe-like machine. The system 200 may be capable of manipulating components in multiple axis. For example, the system 200 may be configured to rotate the elongate substrate 210 (or main spindle) using the clamps 215, 216. One or more carriages may traverse, or move, different components relative to the elongate substrate 210. Non-limiting examples of components held by carriage that may be moved include: a heat source for reflow or thermosetting, a payoff or spool for filaments (or other wires), a dispense head for adhesive or thermoplastic application, a camera or lighting apparatus for visualization or for placement of aids, and any suitable tools (such as cutting or placement tools). In some embodiments, a payoff for filaments may be include one or more of the following: a tensioner fixed or orbitable around the elongate substrate, a driving motor or braking mechanism, a tension measurement and feedback mechanism. In some embodiments, the system 200 may include a laser tool for cutting or marking. In some embodiments, the system 200 may include a radiofrequency (RF) coil for heat generation (e.g., a heater).

In some embodiments, for filament winding, thermoplastic fibers may be applied to the substrate as-extruded, oriented, annealed, or any combination thereof. In the upstream processes used to make filaments prior to wrapping, the properties of those filaments may be modified even though the base material remains the same. For example, forming a thermoplastic filament by solidifying a strand from a molten stream coming out of an extruder may be limited by the melt strength of the polymer. Subsequently processing the resulting fiber without re-melting it may allow it to be oriented to a much smaller cross-section than possible by extrusion alone. This orientation may leave residual stresses or anisotropic properties (i.e., axial stretch when heated), and sometimes a gentle reheat/annealing process near the melt temperature may allow the polymer molecules to realign and reduce the residual stress. Further, metal-drawing stainless steel may create high tensile strengths/stiffnesses, which may also undergo this process to anneal the steel wire to reduce the strength and increase usefulness during catheter assembly, cutting, etc. This process may also be done with metal-drawing stainless steel creating very high tensile strengths/stiffnesses, which can be undesirable-annealing the steel wire reduces the strength which can be useful during catheter assembly, cutting, etc.

The thermoplastic fibers may be provided with a round or flat shape and with the same or different durometers as suitable. An operator, or automatic "tacker" of the system 200, may attach an end of a filament to the elongate substrate 210 at the beginning of a process. Two materials of very different durometers in the form of filaments may be added to the elongate substrate 210. The proportion or location of each filament may be varied by pre-programmed amounts of rotation and axial travel. Reflow, or melting, by a heater may be used to secure end of filaments before cutting them off. The elongate substrate 210 with filament thereon may be removable from the clamps 215, 216 to allow for the addition of a heat shrink material or for reflow by another machine. The system 200 may dispense and cure thermosets or adhesives as suitable.

Although the system 200 is shown with a horizontal longitudinal axis 201, in some embodiments, the axis of the system 200 may be vertical. Auto-clamp and release chucks may be used to allow for vertical dip coating of different materials around the elongate substrate 210. Further, in one or more embodiment, the axis 201 may not be linear, but rather may be curved along a path in 3-dimensions.

The system 200 may be configured to employ an optimal melting behavior of various materials used to form the medical device. In particular, information about the melting behavior of different materials may be used to form an optimal construction sequence. In some embodiments, the system 200 may apply thermosets or higher melt temperature materials initially, which may not be disturbed during subsequent lower-temperature additions or reflows. In some embodiments, the system 200 may use non-melting or high temperature films or fibers as spacers between layers or to secure, or separate, conductors. In some embodiments, the system 200 may use lubricants or release agents between layers to avoid interlayer bonding and preserving flexibility.

In some embodiments, the system 200 may use "striping" for crosshead coating, in which different materials are dispensed or wound, for example, each at different places around the circumference of the elongate substrate 210. For example, two strips of a soft "A" material and two strips of a soft "B" material may be disposed at different places around the circumference of the elongate substrate 210. The use of "striping" for crosshead coating may minimize asymmetric transitions that can cause "whip" or "notchiness" when rotating, may facilitate varying the width of the stripes relative to each other to facilitate very low thicknesses, may facilitate rotating the mandrel relative to the materials to produce spiraled stripes, or may facilitate controlling the length of the transition avoids stress concentrations and spots for kinks or lumen collapses.

Figure 10:
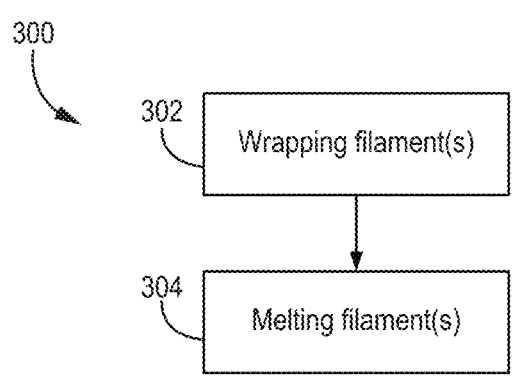
FIG. 10 is a flow diagram that illustrates one example of a method for use with, for example, the additive manufacturing system of FIG. 9.

FIG. 10 shows one example of a method 300 of using the system 200 (e.g., as shown in FIG. 9) for additive manufacturing. The method 300 may be used to manufacture a medical device (e.g., as shown in FIGS. 1-8).

The method 300 may include wrapping 302 a filament around an elongate substrate along a longitudinal direction between a proximal end of the elongate substrate and a distal end of the elongate substrate.

The method 300 may also include melting 304 the filament to form at least a portion of the medical device. In one or more embodiments, an additional filament may be wrapped and melted with the filament.

Illustrative Embodiments

While the present disclosure is not so limited, an appreciation of various aspects of the disclosure will be gained through a discussion of the specific examples and illustrative embodiments provided below. Various modifications of the examples and illustrative embodiments, as well as additional embodiments of the disclosure, will become apparent herein.

A1. A method of manufacturing an elongate medical device, the method comprising:
  wrapping a filament around an elongate substrate along a longitudinal direction between a proximal end of the elongate substrate and a distal end of the elongate substrate; and
  melting the filament to form at least a portion of the elongate medical device.

A2. The method according to embodiment A1, wherein the filament comprises a polymer material.

A3. The method according to embodiment A1 or A2, wherein the filament comprises a thermoplastic material, a thermoset polymeric material, or both.

A4. The method according to any preceding A embodiment, further comprising:
  covering the filament wrapped around the elongate substrate with a tube prior to melting the filament; and
  removing the tube after melting the filament.

A5. The method according to any preceding A embodiment, wherein wrapping the filament around the elongate substrate comprises wrapping the filament more than one turn around the elongate substrate.

A6. The method according to any preceding A embodiment, wherein wrapping the filament around the elongate substrate comprises wrapping the filament to include slack in one or more turns of the filament.

A7. The method according to any preceding A embodiment, further comprising wrapping an additional filament around the elongate substrate between the proximal end and the distal end.

A8. The method according to embodiment A7, wherein wrapping the additional filament around the elongate substrate comprises wrapping the filament to include slack in one or more turns of the additional filament.

A9. The method according to embodiment A7 or A8, further comprising melting the additional filament to form at least a portion of the elongate medical device.

A10. The method according to any one of embodiments A7 to A9, wherein the additional filament comprises one or more of the following: a metal conductor, a polymeric conductor, or an aramid fiber.

A11. The method according to any one of embodiments A7 to A10, wherein wrapping the filament and the additional filament around the elongate substrate comprises positioning the filament and the additional filament adjacent one another and wrapping both the filament and the additional filament together between the proximal end and the distal end.

A12. The method according to any one of embodiments A7 to A10, wherein wrapping the additional filament around the elongate substrate comprises wrapping the additional filament around the filament after wrapping the filament around the elongate substrate.

A13. The method according to any one of embodiments A7 to A12, wherein wrapping the filament around the elongate substrate comprises wrapping the filament at variable pitches along the longitudinal direction, wrapping the additional filament around the elongate substrate at variable pitches along the longitudinal direction, or both.

A14. The method according to embodiment A13, wherein wrapping the filament around the elongate substrate comprises wrapping the filament around the elongate substrate at a decreasing variable pitch from the proximal end to the distal end, and wherein wrapping the additional filament around the elongate substrate comprises wrapping the additional filament around the elongate substrate at an increasing variable pitch from the proximal end to the distal end.

A15. The method according to any one of embodiments A7 to A14, wherein the filament and the additional filament are wrapped around the elongate substrate at different pitches.

A16. The method according to any one of embodiments A1 to A6, wherein wrapping the filament around the elongate substrate comprises wrapping the filament at variable pitches along the longitudinal direction.

A17. The method according to any preceding A embodiment, wherein wrapping the filament around the elongate substrate comprises one or more of the following: braiding, weaving, or knitting the filament around the elongate substrate.

A18. The method according to any preceding A embodiment, further comprising attaching the filament to the elongate substrate at the proximal end of the elongate substrate prior to wrapping the filament.

A19. The method according to embodiment A18, wherein attaching the filament to the elongate substrate comprises melting the filament to the proximal end of the elongate substrate.

A20. The method according to embodiment A18 or A19, wherein attaching the filament to the elongate substrate comprises adhering the filament to the proximal end of the elongate substrate.

A21. The method according to any preceding A embodiment, further comprising pre-wrapping the filament around the elongate substrate at the proximal end of the elongate substrate such that the at least a portion of the filament is wrapped around another portion of the filament to secure the filament to the proximal end of the elongate substrate.

A22. The method according to any preceding A embodiment, further comprising clamping the filament to the proximal end of the elongate substrate prior to wrapping the filament.

A23. The method according to any preceding A embodiment, further comprising selectively adding at least one discrete marker to the filament along the longitudinal direction.

A24. The method according to embodiment A23, wherein the at least one discrete marker comprises a visual indicator or a fluoroscopic indicator.

A25. The method according to any preceding A embodiment, further comprising selectively adding at least one component to the elongate substrate prior to wrapping the filament around the elongate substrate, wherein wrapping the filament around the elongate substrate secures the at least one component to the elongate substrate.

A26. The method according to embodiment A25, wherein the at least one component comprises one or more of the following: an electrode, a marker, a balloon, a connector ring or other electrical contact, or a lumen.

A27. The method according to any preceding A embodiment, further comprising chemically processing the filament before wrapping the filament around the elongate substrate, chemically processing the filament after wrapping the filament around the elongate substrate, or both.

A28. The method according to embodiment A27, wherein chemically processing the filament comprises one or more of the following: cross-linking a thermoset polymer material with heat, coating with a fluid, or curing using light to initiate a reaction.

A29. The method according to any preceding A embodiment, wherein the filament comprises a cross-sectional shape, wherein the cross-sectional shape defines a rounded, rectangular, or square shape.

B1. An additive manufacturing system comprising:
a substrate system comprising a clamp to secure an end portion of an elongate substrate extending along a longitudinal direction;
a filament system comprising one or more spools configured to store one or more filaments;
a heater configured to deliver heat to any of the one or more filaments disposed on the elongate substrate;
one or more actuators to position the one or more filaments relative to the elongate substrate and to position the heater relative to any of the one or more filaments disposed on the elongate substrate; and
a controller operably coupled to the heater and the one or more actuators, the controller configured to:
control the one or more actuators to wrap the one or more filaments around the elongate substrate secured by the substrate system; and
activate the heater to deliver heat to at least one of the one or more filaments disposed on the elongate substrate to melt the at least one of the one or more filaments.

Thus, various embodiments of filament wrapping and reflow system and methods to manufacture an elongate medical device are disclosed. It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

All references and publications cited herein are expressly incorporated herein by reference in their entirety for all purposes, except to the extent any aspect directly contradicts this disclosure.

Unless otherwise indicated, all numbers expressing feature sizes, amounts, and physical properties used in the specification and claims may be understood as being modified either by the term "exactly" or "about." Accordingly, unless indicated to the contrary, the numerical parameters set forth in the foregoing specification and attached claims are approximations that can vary depending upon the desired properties sought to be obtained by those skilled in the art utilizing the teachings disclosed herein or, for example, within typical ranges of experimental error.

As used herein, the term "configured to" may be used interchangeably with the terms "adapted to" or "structured to" unless the content of this disclosure clearly dictates otherwise.

The singular forms "a," "an," and "the" encompass embodiments having plural referents unless its context clearly dictates otherwise.

As used herein, "have," "having," "include," "including," "comprise," "comprising" or the like are used in their open-ended sense, and generally mean "including, but not limited to." It will be understood that "consisting essentially of," "consisting of," and the like are subsumed in "comprising," and the like.

Reference to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout are not necessarily referring to the same embodiment of the disclosure. Furthermore, the particular features, configurations, compositions, or characteristics may be combined in any suitable manner in one or more embodiments.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the disclosure.

The invention claimed is:

1. A method comprising:
wrapping a filament around an elongate medical device substrate to thereby form a distinct thread of wrapped filament, wherein the wrapped filament has a variance along the elongate medical device substrate in one or more of a wrapping pitch, a filament density, a filament thickness, a filament material composition, and a filament cross-sectional shape; and
melting the wrapped filament to thereby form at least a portion of the elongate medical device having a property that varies in accordance with the variance in the wrapped filament.

2. The method of claim 1, wherein the filament comprises a polymer material.

3. The method of claim 1, wherein the filament comprises a thermoplastic material, a thermoset polymeric material, or both.

4. A method comprising:
wrapping a filament around an elongate medical device substrate to thereby form a distinct thread of wrapped filament along a longitudinal direction of the elongate medical device substrate;
melting the wrapped filament to convert the distinct thread to a continuous material to thereby form at least a portion of the elongate medical device;
covering the wrapped filament with a tube prior to melting the wrapped filament; and
removing the tube after melting the wrapped filament.

5. The method of claim 1, wherein wrapping the filament around the elongate medical device substrate comprises wrapping the filament more than one turn around the elongate medical device substrate.

6. A method comprising:
wrapping a filament at variable pitches in a longitudinal direction around an elongate medical device substrate to thereby form a distinct thread of wrapped filament; and
melting the wrapped filament to convert the distinct thread to a continuous material to thereby form at least a portion of the elongate medical device,
wherein wrapping the filament around the elongate medical device substrate comprises wrapping the filament to include slack in one or more turns of the filament.

7. The method of claim 1, further comprising
wrapping an additional filament around the wrapped filament prior to, during, or after melting the wrapped filament.

8. The method of claim 7, further comprising melting the additional filament to form at least a portion of the elongate medical device.

9. The method of claim 7, wherein the additional filament comprises one or more of the following: a metal conductor, a polymeric conductor, or an aramid fiber.

10. The method of claim 7, wherein wrapping the filament and the additional filament around the elongate medical device substrate comprises positioning the filament and the additional filament adjacent one another and wrapping both the filament and the additional filament together.

11. The method of claim 7, wherein wrapping the filament around the elongate medical device substrate comprises wrapping the filament at variable pitches along the longitudinal direction, wrapping the additional filament around the elongate medical device substrate at variable pitches along the longitudinal direction, or both.

12. The method of claim 7, wherein the filament and the additional filament are wrapped around the elongate medical device substrate at different pitches.

13. The method of claim 1, further comprising attaching the filament to the elongate medical device substrate prior to wrapping the filament.

14. The method of claim 1, further comprising pre-wrapping the filament around the elongate medical device substrate such that at least a portion of the filament is wrapped around another portion of the filament to secure the filament to the elongate medical device substrate.

15. The method of claim 1, further comprising clamping the filament to the elongate medical device substrate prior to wrapping the filament.

16. The method of claim 1, further comprising selectively adding at least one discrete marker to the filament along the longitudinal direction.

17. The method of claim 1, further comprising selectively adding at least one component to the elongate medical device substrate prior to wrapping the filament around the elongate substrate so that the wrapped filament secures the at least one component to the elongate medical device substrate.

18. The method of claim 17, wherein the at least one component comprises one or more of the following: an electrode, a marker, a balloon, a connector ring or other electrical contact, or a lumen.

19. The method of claim 1, further comprising chemically processing the filament before wrapping the filament around the elongate medical device substrate, chemically processing the filament after wrapping the filament around the elongate medical device substrate, or both.

20. The method of claim 19, wherein chemically processing the filament comprises one or more of the following: cross-linking a thermoset polymer material with heat, coating with a fluid, or curing using light to initiate a reaction.

* * * * *